United States Patent [19]

Schmetzer et al.

[11] Patent Number: 4,470,984

[45] Date of Patent: Sep. 11, 1984

[54] COMBATING PESTS WITH NOVEL OXIME-CARBAMATES

[75] Inventors: Johannes Schmetzer, Cologne; Jörg Stetter, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 343,132

[22] Filed: Jan. 27, 1982

[30] Foreign Application Priority Data

Feb. 14, 1981 [DE] Fed. Rep. of Germany ....... 3105400

[51] Int. Cl.$^3$ .................... A01N 43/08; A01N 43/10; A01N 43/16; A01N 43/20
[52] U.S. Cl. .................... 424/248.51; 260/453.3; 260/453.8; 424/298; 424/275; 549/424; 549/480; 549/510; 549/511; 549/28; 549/68; 549/88
[58] Field of Search .................... 260/453.3, 453.8; 424/298, 248.51, 275; 549/424, 480, 510, 511, 28, 68, 88

[56] References Cited

U.S. PATENT DOCUMENTS 3,655,758   4/1972   Kurhajec et al. ................ 260/453.8

FOREIGN PATENT DOCUMENTS 2621102   11/1977   Fed. Rep. of Germany .

Primary Examiner—Henry R. Jiles
Assistant Examiner—Robert C. Whittenbaugh
Attorney, Agent, or Firm—Sprung Horn Kramer & Woods

[57] ABSTRACT

An N-sulphenylated oxime-carbamate of the formula

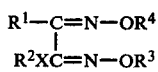

in which
R$^1$ is optionally substituted alkyl, cycloalkyl, aryl or aralkyl,
R$^2$ is alkyl, alkenyl or alkynyl, or
R$^1$ and R$^2$ together are an alkylene bridge having 1-6 C atoms, one of R$^3$ and R$^4$ is the radical

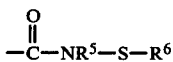

and the other is alkyl, alkenyl, alkynyl, halogenoalkyl, halogenoalkenyl or alkoxyalkyl,
R$^5$ is alkyl,
R$^6$ is alkyl, halogenoalkyl, optionally substituted phenyl, alkoxycarbonyl or dialkylamino, NR$^8$—SO$_2$ R$^7$, or a radical identical to the radical to which the grouping —S—R$^6$ is bonded,
R$^7$ is alkyl, dialkylamino or optionally substituted phenyl,
R$^8$ is alkyl, and
X is O or S,
which possesses pesticidal activity.

4 Claims, No Drawings

COMBATING PESTS WITH NOVEL OXIME-CARBAMATES

The present invention relates to certain new N-sulphenylated oxime-carbamates, to a process for their preparation and to their use in pest-combating agents.

It has already been disclosed that methylthio-substituted oxime-carbamates, such as 3,3-dimethyl-2-methyl-carbamoyloximino-1-methylthio-butane (see Deutsche Offenlegungsschrift (German Published Specification) No. 2,216,838) or 1-methylcarbamoyloximino-1-methylthio-ethane (see Deutsche Offenlegungsschrift (German Published Specification) No. 1,567,142), have insecticidal and acaricidal properties. However, these compounds are not completely satisfactory, especially when low concentrations are employed.

The present invention now provides, as new compounds, the N-sulphenylated oxime-carbamates of the general formula

in which
R$^1$ represents alkyl, cycloalkyl, aryl or aralkyl, each of which may be optionally substituted,
R$^2$ represents alkyl, alkenyl or alkynyl, or
R$^1$ and R$^2$ together represent an alkylene bridge having 1–6 C atoms, and one of R$^3$ and R$^4$ represents the radical

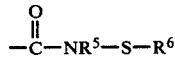

while the other of R$^3$ and
R$^4$ represents an alkyl, alkenyl, alkynyl, halogenoalkyl, halogenoalkenyl or alkoxyalkyl,
R$^5$ represents alkyl, and
R$^6$ represents alkyl, halogenoalkyl, optionally substituted phenyl, alkoxycarbonyl or dialkylamino, or represents a radical identical to that to which the grouping —S—R$^6$ is bonded or represents the grouping —NR$^8$—SO$_2$—R$^7$,
wherein
R$^7$ represents alkyl, dialkylamino or optionally substituted phenyl and
R$^8$ represents alkyl, and
X represents O or S.

The compounds of the formula (I) can occur in the syn form or anti form, but are predominantly produced as mixtures of both forms.

The invention also provides a process for the preparation of an N-sulphenylated oxime-carbamate of the formula (I) in which
(a) an oxime of the general formula

in which
R$^1$, R$^2$ and X have the meanings given above and one of R$^9$ and R$^{10}$ represents H and the other of R$^9$ and R$^{10}$ represents alkyl, alkenyl, alkynyl, halogenoalkyl, halogenoalkenyl or alkoxyalkyl, is reacted with a sulphenylated carbamoyl halide of the general formula

in which
R$^5$ and R$^6$ have the meanings given above and
Hal represents fluorine or chlorine,
in the presence of a diluent and an acid-binding agent,
or (b) an oxime-carbamate of the general formula

in which
R$^1$, R$^2$ and X have the meanings given above, one of R$^{11}$ and R$^{12}$ represents the radical

while the other of R$^{11}$ and R$^{12}$ represents alkyl, alkenyl, alkynyl, halogenoalkyl, halogenoalkenyl or alkoxyalkyl,
R$^5$ represents alkyl and
X represents O or S,
is reacted with a sulphenyl chloride of the general formula

in which
R$^6$ has the meaning given above,
in the presence of a diluent and of an acid-binding agent.

The compounds of the formula (I) are suitable for combating pests and have, in particular, powerful insecticidal, acaricidal and nematicidal properties.

Surprisingly, the compounds of the formula (I) exhibit a greater insecticidal and acaricidal action than similar known compounds with the same type of action.

Formula (I) gives a general definition of the N-sulphenylated oxime-carbamates according to the invention. In this formula, R$^1$ preferably represents alkyl having 1 to 4 carbon atoms, halogenoalkyl having 1 to 4 carbon atoms and up to 5 halogen atoms (especially fluorine, chlorine or bromine), cycloalkyl having up to 8 carbon atoms, alkoxyalkyl or alkylthioalkyl having in either case up to 3 C atoms in each alkyl part, or optionally substituted phenyl, the substituent(s) preferably being selected from halogen, (especially fluorine, chlorine and bromine), cyano, nitro and alkyl having 1 to 2 carbon atoms.

R$^2$ preferably represents alkyl having 1 to 4 carbon atoms, alkenyl having 2 to 4 carbon atoms or alkynyl having 2 to 4 carbon atoms.

R$^1$ and R$^2$ together may alternatively represent an optionally methyl-substituted methylene, ethylene or propylene bridge.

R$^3$ or R$^4$ preferably represents alkyl having 1 to 4 carbon atoms, alkenyl having 2 to 4 carbon atoms, alkynyl having 2 to 4 carbon atoms, halogenoalkyl having 1 to 4 carbon atoms and up to 5 halogen atoms, halogenoalkenyl having 2 to 4 carbon atoms and up to 5 halogen atoms, alkoxyalkyl having up to 2 carbon atoms in each alkyl part, or the radical

(in this formula, one of $R^3$ and $R^4$ must represent the radical

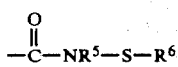

in each case).

$R^5$ preferably represents methyl or ethyl.

$R^6$ preferably represents alkyl having 1 to 4 carbon atoms, or halogenoalkyl having 1 to 2 carbon atoms and up to 5 halogen atoms (especially fluorine atoms and chlorine atoms, trifluoromethyl, chlorodifluoromethyl, dichlorofluoromethyl and trichloromethyl being mentioned as examples of such halogenoalkyl groups), or optionally substituted phenyl, the substituent(s) preferably being selected from halogen (especially fluorine, chlorine or bromine), alkyl having 1 to 2 carbon atoms and halogenoalkyl having 1 to 2 carbon atoms and up to 5 halogen atoms (especially fluorine atoms and chlorine atoms, trifluoromethyl being mentioned as an example). $R^6$ also preferably represents alkoxycarbonyl having 1 to 4 carbon atoms in the alkoxy part, dialkylamino having 1 to 4 carbon atoms in each alkyl part, or a radical identical to the radical to which the grouping —S—$R^6$ is bonded. $R^6$ also preferably represents the radical —$NR^8$—$SO_2R^7$, wherein $R^8$ represents alkyl having 1 to 4 carbon atoms and $R^7$ represents $C_{1-4}$ alkyl, dialkylamino having 1 to 4 carbon atoms in each alkyl part or optionally substituted phenyl, the substituent(s) preferably being selected from halogen (especially fluorine, chlorine or bromine), alkyl having 1 to 2 carbon atoms, halogenoalkyl having 1 to 2 carbon atoms and up to 5 halogen atoms (especially fluorine atoms and chlorine atoms, trifluoromethyl being mentioned as an example), cyano and nitro.

X represents S or O in the preferred compounds.

Very particularly preferred N-sulphenylated oxime-carbamates of the formula (I) are those in which $R^1$ represents methyl, isopropyl, tert.-butyl, fluoro-tert.-butyl, chloro-tert.-butyl, difluoro-tert.-butyl or dichloro-tert.-butyl, $R^2$ represents methyl or ethyl, or $R^1$ and $R^2$ together represent an ethylene bridge, $R^3$ and $R^4$ represent methyl, ethyl, allyl, propargyl or

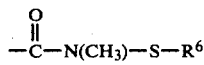

(in this formula, one of $R^3$ and $R^4$ must represent

in each case), and $R^6$ represents trichloromethyl, dichlorofluoromethyl, phenyl which is substituted by halogenoalkyl or by alkyl, or a radical identical to the radical to which the grouping —S—$R^6$ is bonded. X preferably represents S.

In addition to the compounds mentioned in the preparative examples, the following compounds may be individually mentioned:

TABLE 1

TABLE 1-continued $$R^1-C=N-O-R^4$$
$$R^2S-C=N-O-R^3 \quad (I)$$

| | $R^1$ | $R^2$ | $R^3$ | $R^4$ | |
|---|---|---|---|---|---|
| " | | CH₃ | —CH₂—CH=CH₂ | " | " |
| " | | C₂H₅ | CH₃ | " | " |
| " | | C₂H₅ | C₂H₅ | " | " |
| " | | C₂H₅ | —CH₂—C≡CH | " | " |
| " | | C₂H₅ | —CH₂—CH=CH₂ | " | " |

| $R^1 + R^2$ | $R^3$ | $R^4$ | $R^6$ |
|---|---|---|---|
| —C(CH₃)₂—CH₂— | CH₃ | —C(=O)—N(CH₃)—S—R⁶ | CCl₃ |
| " | C₂H₅ | " | " |
| " | CH₃ | " | CCl₂F |
| " | C₂H₅ | " | " |
| " | CH₃ | " | dimeric |
| " | C₂H₅ | " | " |
| —CH₂—CH₂— | CH₃ | " | CCl₃ |
| " | C₂H₅ | " | " |
| " | CH₃ | " | CCl₂F |
| " | C₂H₅ | " | " |
| " | CH₃ | " | —C₆H₄—Cl |
| " | C₂H₅ | " | " |
| " | " | " | dimeric |
| " | " | " | " |

| $R^1$ | $R^2$ | $R^3$ | $R^4$ | $R^6$ |
|---|---|---|---|---|
| (CH₃)₂HC— | CH₃ | CH₃ | —C(=O)—N(CH₃)—S—R⁶ | CCl₃ |
| " | CH₃ | C₂H₅ | " | " |
| " | CH₃ | —CH₂—C≡CH | " | " |
| " | CH₃ | —CH₂—CH=CH₂ | " | " |
| " | C₂H₅ | CH₃ | " | " |
| " | C₂H₅ | C₂H₅ | " | " |
| " | C₂H₅ | —CH₂—C≡CH | " | " |
| " | C₂H₅ | —CH₂—CH=CH₂ | " | " |
| " | CH₃ | CH₃ | " | CCl₂F |
| " | CH₃ | C₂H₅ | " | " |
| " | CH₃ | —CH₂—C≡CH | " | " |
| " | CH₃ | —CH₂—CH=CH₂ | " | " |
| " | C₂H₅ | CH₃ | " | " |
| " | C₂H₅ | C₂H₅ | " | " |
| " | C₂H₅ | —CH₂—C≡CH | " | " |
| " | C₂H₅ | —CH₂—CH=CH₂ | " | " |
| " | CH₃ | CH₃ | " | —C₆H₄—Cl |
| " | CH₃ | C₂H₅ | " | " |
| " | CH₃ | —CH₂—C≡CH | " | " |
| " | CH₃ | —CH₂—CH=CH₂ | " | " |
| " | C₂H₅ | CH₃ | " | " |
| " | C₂H₅ | C₂H₅ | " | " |
| " | C₂H₅ | —CH₂—C≡CH | " | " |
| " | C₂H₅ | —CH₂—CH=CH₂ | " | " |
| " | CH₃ | CH₃ | " | dimeric |
| " | CH₃ | C₂H₅ | " | " |
| " | CH₃ | —CH₂—C≡CH | " | " |
| " | CH₃ | —CH₂—CH=CH₂ | " | " |
| " | C₂H₅ | CH₃ | " | " |
| " | C₂H₅ | C₂H₅ | " | " |
| " | C₂H₅ | —CH₂—C≡CH | " | " |
| " | C₂H₅ | —CH₂—CH=CH₂ | " | " |
| CH₃S—C(CH₃)₂— | CH₃ | CH₃ | " | CCl₃ |

TABLE 1-continued

| | $R^1$—C=N—O—$R^4$ <br> $R^2S$—C=N—O—$R^3$ | | (I) | |
|---|---|---|---|---|
| " | CH₃ | C₂H₅ | " | " |
| " | C₂H₅ | CH₃ | " | " |
| " | C₂H₅ | C₂H₅ | " | " |
| " | CH₃ | CH₃ | " | CCl₂F |
| " | CH₃ | C₂H₅ | " | " |
| " | C₂H₅ | CH₃ | " | " |
| " | C₂H₅ | C₂H₅ | " | " |
| " | CH₃ | CH₃ | " |  |
| " | CH₃ | C₂H₅ | " | " |
| " | C₂H₅ | CH₃ | " | " |
| " | C₂H₅ | C₂H₅ | " | " |
| " | CH₃ | CH₃ | " | dimeric |
| " | CH₃ | C₂H₅ | " | " |
| " | C₂H₅ | CH₃ | " | " |
| " | C₂H₅ | C₂H₅ | " | " |
| FCH₂—C(CH₃)₂— | CH₃ | CH₃ | " | CCl₃ |
| " | CH₃ | C₂H₅ | " | " |
| " | C₂H₅ | CH₃ | " | " |
| " | C₂H₅ | C₂H₅ | " | " |
| " | CH₃ | CH₃ | " | CCl₂F |
| " | CH₃ | C₂H₅ | " | " |
| " | C₂H₅ | CH₃ | " | " |
| " | C₂H₅ | C₂H₅ | " | " |
| " | CH₃ | CH₃ | " | 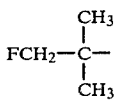 |
| " | CH₃ | C₂H₅ | " | " |
| " | C₂H₅ | CH₃ | " | " |
| " | C₂H₅ | C₂H₅ | " | " |
| " | CH₃ | CH₃ | " | dimeric |
| " | CH₃ | C₂H₅ | " | " |
| " | C₂H₅ | CH₃ | " | " |
| " | C₂H₅ | C₂H₅ | " | " |
| ClCH₂—C(CH₃)₂— | CH₃ | CH₃ | " | CCl₃ |
| " | CH₃ | C₂H₅ | " | " |
| " | C₂H₅ | CH₃ | " | " |
| " | C₂H₅ | C₂H₅ | " | " |
| " | CH₃ | CH₃ | " | CCl₂F |
| " | CH₃ | C₂H₅ | " | " |
| " | C₂H₅ | CH₃ | " | " |
| " | C₂H₅ | C₂H₅ | " | " |
| " | CH₃ | CH₃ | " |  |
| " | CH₃ | C₂H₅ | " | " |
| " | C₂H₅ | CH₃ | " | " |
| " | C₂H₅ | C₂H₅ | " | " |
| " | CH₃ | CH₃ | " | dimeric |
| " | CH₃ | C₂H₅ | " | " |
| " | C₂H₅ | CH₃ | " | " |
| " | C₂H₅ | C₂H₅ | " | " |
| FCH₂—C(CH₂F)(CH₃)— | CH₃ | CH₃ | " | CCl₃ |

TABLE 1-continued $$\begin{array}{c} R^1-C=N-O-R^4 \\ | \\ R^2S-C=N-O-R^3 \end{array} \quad (I)$$

| R¹ | R² | R³ | R⁴ | (last) |
|---|---|---|---|---|
| " | CH₃ | C₂H₅ | " | " |
| " | C₂H₅ | CH₃ | " | " |
| " | C₂H₅ | C₂H₅ | " | " |
| " | CH₃ | CH₃ | " | CCl₂F |
| " | CH₃ | C₂H₅ | " | " |
| " | C₂H₅ | CH₃ | " | " |
| " | C₂H₅ | C₂H₅ | " | " |
| " | CH₃ | CH₃ | " | ⟨○⟩—Cl |
| " | CH₃ | C₂H₅ | " | " |
| " | C₂H₅ | CH₃ | " | " |
| " | C₂H₅ | C₂H₅ | " | " |
| " | CH₃ | CH₃ | " | dimeric |
| " | CH₃ | C₂H₅ | " | " |
| " | C₂H₅ | CH₃ | " | " |
| " | C₂H₅ | C₂H₅ | " | " |
| CH₃ | CH₃ | CH₃ | " | CCl₃ |
| " | CH₃ | C₂H₅ | " | " |
| " | CH₃ | —CH₂—C≡CH | " | " |
| " | CH₃ | —CH₂—CH=CH₂ | " | " |
| " | C₂H₅ | CH₃ | " | " |
| " | C₂H₅ | C₂H₅ | " | " |
| " | C₂H₅ | —CH₂—C≡CH | " | " |
| " | C₂H₅ | —CH₂—CH=CH₂ | " | " |
| " | CH₃ | CH₃ | " | CCl₂F |
| " | CH₃ | C₂H₅ | " | " |
| " | CH₃ | —CH₂—C≡CH | " | " |
| " | CH₃ | —CH₂—CH=CH₂ | " | " |
| " | C₂H₅ | CH₃ | " | " |
| " | C₂H₅ | C₂H₅ | " | " |
| " | C₂H₅ | —CH₂—C≡CH | " | " |
| " | C₂H₅ | —CH₂—CH=CH₂ | " | " |
| " | CH₃ | CH₃ | " | ⟨○⟩—Cl |
| " | CH₃ | C₂H₅ | " | " |
| " | CH₃ | —CH₂—C≡CH | " | " |
| " | CH₃ | —CH₂—CH=CH₂ | " | " |
| " | C₂H₅ | CH₃ | " | " |
| " | C₂H₅ | C₂H₅ | " | " |
| " | C₂H₅ | —CH₂—C≡CH | " | " |
| " | C₂H₅ | —CH₂—CH=CH₂ | " | " |
| " | CH₃ | CH₃ | " | dimeric |
| " | CH₃ | C₂H₅ | " | " |
| " | CH₃ | —CH₂—C≡CH | " | " |
| " | CH₃ | —CH₂—CH=CH₂ | " | " |
| " | C₂H₅ | CH₃ | " | " |
| " | C₂H₅ | C₂H₅ | " | " |
| " | C₂H₅ | —CH₂—C≡CH | " | " |
| " | C₂H₅ | —CH₂—CH=CH₂ | " | " |
| (CH₃)₃C— | CH₃ | $\begin{array}{c}O\ CH_3\\ \|\ \ |\\ -C-N-S-R^6\end{array}$ | CH₃ | CCl₃ |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |
| " | C₂H₅ | " | —CH₂—CH=CH₂ | " |
| " | CH₃ | " | CH₃ | CCl₂F |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |
| " | C₂H₅ | " | —CH₂—CH=CH₂ | " |
| " | CH₃ | " | CH₃ | ⟨○⟩—Cl |

TABLE 1-continued $$R^1-C=N-O-R^4$$
$$R^2S-C=N-O-R^3 \quad (I)$$

| | | | | |
|---|---|---|---|---|
| " | CH₃ " | | C₂H₅ | " |
| " | CH₃ " | | —CH₂—C≡CH | " |
| " | CH₃ " | | —CH₂—CH=CH₂ | " |
| " | C₂H₅ " | | CH₃ | " |
| " | C₂H₅ " | | C₂H₅ | " |
| " | C₂H₅ " | | —CH₂—C≡CH | " |
| " | C₂H₅ " | | —CH₂—CH=CH₂ | " |
| " | CH₃ " | | CH₃ | dimeric |
| " | CH₃ " | | C₂H₅ | " |
| " | CH₃ " | | —CH₂—C≡CH | " |
| " | CH₃ " | | —CH₂—CH=CH₂ | " |
| " | C₂H₅ " | | CH₃ | " |
| " | C₂H₅ " | | C₂H₅ | " |
| " | C₂H₅ " | | —CH₂—C≡CH | " |
| " | C₂H₅ " | | —CH₂—CH=CH₂ | " |

| R¹ + R² | R³ | R⁴ | R⁶ |
|---|---|---|---|
| $\begin{array}{c}CH_3\\|\\-C-CH_2-\\|\\CH_3\end{array}$ | $\begin{array}{cc}O & CH_3\\||&|\\-C-N-S-R^6\end{array}$ | CH₃ | CCl₃ |
| " | " | C₂H₅ | " |
| " | " | CH₃ | CCl₂F |
| " | " | C₂H₅ | " |
| " | " | CH₃ | ⟨○⟩—Cl |
| " | " | C₂H₅ | " |
| " | " | CH₃ | dimeric |
| " | " | C₂H₅ | " |
| —CH₂—CH₂— | " | CH₃ | CCl₃ |
| " | " | C₂H₅ | " |
| " | " | CH₃ | CCl₂F |
| " | " | C₂H₅ | " |
| " | " | CH₃ | ⟨○⟩—Cl |
| " | " | C₂H₅ | " |
| " | " | CH₃ | dimeric |
| " | " | C₂H₅ | " |

| R¹ | R² | R³ | R⁴ | R⁶ |
|---|---|---|---|---|
| (CH₃)₂HC— | CH₃ | $\begin{array}{cc}O & CH_3\\||&|\\-C-N-S-R^6\end{array}$ | CH₃ | CCl₃ |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |
| " | C₂H₅ | " | —CH₂—CH=CH₂ | " |
| " | CH₃ | " | CH₃ | CCl₂F |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |
| " | C₂H₅ | " | —CH₂—CH=CH₂ | " |
| " | CH₃ | " | CH₃ | ⟨○⟩—Cl |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |

TABLE 1-continued $$R^1-C=N-O-R^4$$
$$R^2S-C=N-O-R^3 \quad (I)$$

| $R^1$ | $R^2$ | | $R^3$ | $R^4$ |
|---|---|---|---|---|
| " | $C_2H_5$ | " | $-CH_2-CH=CH_2$ | " |
| " | $CH_3$ | " | $CH_3$ | dimeric |
| " | $CH_3$ | " | $C_2H_5$ | " |
| " | $CH_3$ | " | $-CH_2-C\equiv CH$ | " |
| " | $CH_3$ | " | $-CH_2-CH=CH_2$ | " |
| " | $C_2H_5$ | " | $CH_3$ | " |
| " | $C_2H_5$ | " | $C_2H_5$ | " |
| " | $C_2H_5$ | " | $-CH_2-C\equiv CH$ | " |
| " | $C_2H_5$ | " | $-CH_2-CH=CH_2$ | " |
| $CH_3S-C(CH_3)_2-CH_3$...  | $CH_3$ | " | $CH_3$ | $CCl_3$ |
| " | $CH_3$ | " | $C_2H_5$ | " |
| " | $C_2H_5$ | " | $CH_3$ | " |
| " | $C_2H_5$ | " | $C_2H_5$ | " |
| " | $CH_3$ | " | $CH_3$ | $CCl_2F$ |
| " | $CH_3$ | " | $C_2H_5$ | " |
| " | $C_2H_5$ | " | $CH_3$ | " |
| " | $C_2H_5$ | " | $C_2H_5$ | " |
| " | $CH_3$ | " | $CH_3$ | ⟨phenyl⟩-Cl |
| " | $CH_3$ | " | $C_2H_5$ | " |
| " | $C_2H_5$ | " | $CH_3$ | " |
| " | $C_2H_5$ | " | $C_2H_5$ | " |
| " | $CH_3$ | " | $CH_3$ | dimeric |
| " | $CH_3$ | " | $C_2H_5$ | " |
| " | $C_2H_5$ | " | $CH_3$ | " |
| " | $C_2H_5$ | " | $C_2H_5$ | " |
| $FCH_2-C(CH_3)_2-$  | $CH_3$ | " | $C_2H_5$ | $CCl_3$ |
| " | $C_2H_5$ | " | $CH_3$ | " |
| " | $C_2H_5$ | " | $C_2H_5$ | " |
| " | $CH_3$ | " | " | $CCl_2F$ |
| " | $C_2H_5$ | " | $CH_3$ | " |
| " | $C_2H_5$ | " | $C_2H_5$ | " |
| " | $CH_3$ | " | " | ⟨phenyl⟩-Cl |
| " | $CH_3$ | " | " | " |
| " | $C_2H_5$ | " | $CH_3$ | " |
| " | $C_2H_5$ | " | $C_2H_5$ | " |
| " | $CH_3$ | " | $CH_3$ | dimeric |
| " | $CH_3$ | " | $C_2H_5$ | " |
| " | $C_2H_5$ | " | $CH_3$ | " |
| " | $C_2H_5$ | " | $C_2H_5$ | " |
| $ClCH_2-C(CH_3)_2-$  | $CH_3$ | " | $CH_3$ | $CCl_3$ |
| " | $CH_3$ | " | $C_2H_5$ | " |
| " | $C_2H_5$ | " | $CH_3$ | " |
| " | $C_2H_5$ | " | $C_2H_5$ | " |
| " | $CH_3$ | " | $CH_3$ | $CCl_2F$ |
| " | $CH_3$ | " | $C_2H_5$ | " |
| " | $C_2H_5$ | " | $CH_3$ | " |
| " | $C_2H_5$ | " | $C_2H_5$ | " |
| " | $CH_3$ | " | $CH_3$ | ⟨phenyl⟩-Cl |
| " | $CH_3$ | " | $C_2H_5$ | " |

TABLE 1-continued $$R^1-C=N-O-R^4$$
$$R^2S-C=N-O-R^3 \quad (I)$$

| R¹ | R² | R⁴ | R³ | |
|---|---|---|---|---|
| " | C₂H₅ | " | CH₃ | " |
| " | C₂H₅ | " | C₂H₅ | " |
| " | CH₃ | " | CH₃ | dimeric |
| " | CH₃ | " | C₂H₅ | " |
| " | C₂H₅ | " | CH₃ | " |
| " | C₂H₅ | " | C₂H₅ | " |
| FCH₂—C(CH₂F)(CH₃)— | CH₃ | " | CH₃ | CCl₃ |
| " | CH₃ | " | C₂H₅ | " |
| " | C₂H₅ | " | CH₃ | " |
| " | C₂H₅ | " | C₂H₅ | " |
| " | CH₃ | " | CH₃ | ⟨phenyl⟩—Cl |
| " | CH₃ | " | C₂H₅ | " |
| " | C₂H₅ | " | CH₃ | " |
| " | C₂H₅ | " | C₂H₅ | " |
| " | CH₃ | " | CH₃ | dimeric |
| " | CH₃ | " | C₂H₅ | " |
| " | C₂H₅ | " | CH₃ | " |
| " | C₂H₅ | " | C₂H₅ | " |
| CH₃ | CH₃ | " | CH₃ | CCl₃ |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |
| " | C₂H₅ | " | —CH₂—CH=CH₂ | " |
| " | CH₃ | " | CH₃ | CCl₂F |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |
| " | C₂H₅ | " | —CH₂—CH=CH₂ | " |
| " | CH₃ | " | CH₃ | ⟨phenyl⟩—Cl |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |
| " | C₂H₅ | " | —CH₂—CH=CH₂ | " |
| " | CH₃ | " | CH₃ | dimeric |
| " | CH₃ | " | C₂H₅ | " |
| " | CH₃ | " | —CH₂—C≡CH | " |
| " | CH₃ | " | —CH₂—CH=CH₂ | " |
| " | C₂H₅ | " | CH₃ | " |
| " | C₂H₅ | " | C₂H₅ | " |
| " | C₂H₅ | " | —CH₂—C≡CH | " |
| " | C₂H₅ | " | —CH₂—CH=CH₂ | " |

If 3,3-dimethyl-1-methoximino-1-methylmercapto-butan-2-one oxime and N-methyl-N-dichlorofluoromethylmercapto-carbamoyl fluoride are used as starting materials in process variant (a), the course of the reaction can be represented by the following equation:

$$(CH_3)_3C-C\begin{matrix}\nearrow NOH \\ \searrow C\diagdown NOCH_3 \\ \phantom{xxx}SCH_3\end{matrix} + F-CO-N\begin{matrix}\diagup CH_3 \\ \diagdown SCCl_2F\end{matrix} \longrightarrow$$

-continued

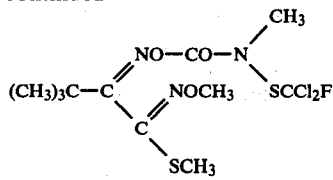

If 1-methylthio-1-oximino-2-methoximinopropane and N,N'-bis-(fluorocarbonyl)-thio-bis-methylamine are used as starting materials in process variant (a), the course of the reaction can be represented by the following equation:

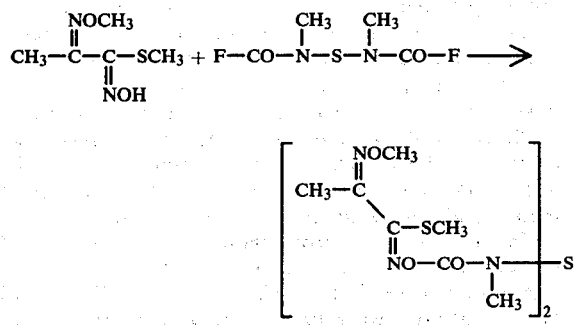

If 1-methylthio-1-methylcarbamoyl-oximino-2-methoximino-propane and 4-chlorophenyl-sulphenyl chloride are used as starting materials in process variant (b), the course of the reaction can be represented by the following equation:

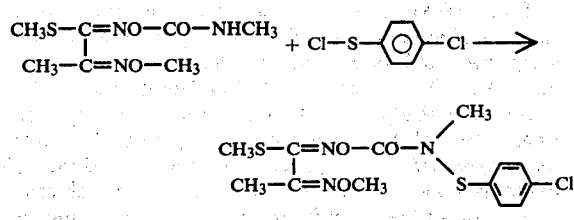

Any of the inert organic solvents are suitable diluents for the reactions according to process variants (a) and (b). These include, as preferences, hydrocarbons, such as toluene or cyclohexane; ketones, such as diethyl ketone and, in particular, acetone or methyl ethyl ketone; nitriles, such as propionitrile and, in particular, acetonitrile; ethers, such as tetrahydrofuran or dioxane; formamides, such as, in particular, dimethylformamide; and halogenated hydrocarbons, such as methylene chloride, carbon tetrachloride or chloroform.

The reactions according to process variants (a) and (b) are carried out in the presence of an acid-binding agent. Any of the inorganic or organic acid-binding agents which can be customarily used can be added. These include, as preferences, alkali metal carbonates, for example sodium carbonate, potassium carbonate and sodium bicarbonate, or lower tertiary alkylamines, cycloalkylamines or arylalkylamines, for example triethylamine, N,N-dimethylbenzylamine and dicyclohexylamine, as well as pyridine and diazabicyclo-octane.

The reaction temperatures can be varied within a wide range. In general, the reaction is carried out at a temperature between 0° and 100° C., preferably between 10° and 80° C. in process variant (a) and preferably between 10° and 50° C. in process variant (b).

In carrying out process variant (a), 1 to 2 mols, or in the case of a dimeric product 0.5 mol, of a carbamoyl halide (III) and 1 to 2 mols of an acid-binding agent are preferably employed per mol of the compound (II).

In carrying out process variant (b), the starting materials are preferably employed in equimolar quantities.

The isolation of the compounds of the formula (I) may be effected in either process variant by customary methods.

Formula (II) gives a general definition of the oximes to be used as starting materials for process variant (a). Preferred oximes of the formula (II) are those in which $R^1$, $R^2$ and X have the preferred and particularly preferred meanings given for the compounds of the formula (I).

$R^9$ or $R^{10}$ preferably represent $C_{1-4}$ alkyl, $C_{2-4}$ alkenyl, $C_{2-4}$ alkynyl, $C_{1-4}$ halogenoalkyl, having up to 3 halogen atoms, alkoxyalkyl having up to 2 C atoms in each alkyl part, and hydrogen (in this formula, only one of $R^9$ and $R^{10}$ may represent hydrogen in each case).

$R^9$ or $R^{10}$ particularly preferably represent methyl, ethyl, propargyl, allyl or hydrogen (only one of $R^9$ and $R^{10}$ being permitted to represent hydrogen).

Some of the oximes of the formula (II) are obtained by a process in which ketones of the general formula

(VI)

wherein $R^9$ represents hydrogen, are reacted with hydroxylaminoethers, or salts thereof, of the general formula

(VII), in which $R^{10}$ has the meaning given above and

Hal represents halogen, particularly chlorine, in the presence of an organic solvent, for example ethanol, and, if appropriate, in the presence of an auxiliary base, for example sodium acetate, at temperatures between 20° C. and 120° C., preferably between 50° and 100° C. The isolation of the compounds (II) is effected in the customary manner, for example by adding water to the reaction mixture and filtering off the precipitate. If necessary, the oximes can also be purified by recrystallization.

Some of the oximes of the formula (II) are obtained by a process in which the ketones of the formula (VI), in which $R^9$ has the meaning given under $R^{10}$, are reacted with hydroxylamine or its salts, in the presence of an organic solvent, for example ethanol, and, if appropriate, in the presence of an auxiliary base, for example sodium acetate, at temperatures between 20° C. and 120° C., preferably between 50° and 100° C. The isolation of the compounds (II) is effected in a customary manner, for example by adding water to the reaction mixture and filtering off the precipitate. If necessary, the oximes can also be purified by recrystallization.

A previous application U.S. Ser. No. 307,337 filed Sept. 30, 1981, corresponding to German Patent Application No. P 30 39 269.9) relates to the oximes of the formula (II).

Formula (III) gives a general definition of the sulphenylated carbamoyl halides which are additionally required as starting materials for the reaction in process variant (a). In this formula, $R^5$ preferably represents methyl or ethyl.

$R^6$ preferably represents alkyl having 1 to 4 carbon atoms, halogenoalkyl having 1 to 2 carbon atoms and up to 5 halogen atoms (such as, in particular, fluorine atoms and chlorine atoms, trifluoromethyl, chlorodifluoromethyl, dichloro-fluoromethyl and trichloromethyl being mentioned as examples), optionally substituted phenyl (preferred substituents being halogen, particularly fluorine, chlorine or bromine, alkyl having 1 to 2 carbon atoms and halogenoalkyl having 1 to 2 carbon atoms and up to 5 halogen atoms, such as, in particular, fluorine atoms and chlorine atoms, the trifluromethyl group being mentioned as an example), alkoxycarbonyl having 1 to 4 carbon atoms in the alkoxy part, and also the identical radical to which the grouping —S—$R^6$ is bonded. $R^6$ also preferably represents the radical —NR$^8$—SO$_2$—R$^7$, wherein $R^8$ represents alkyl having 1 to 4 carbon atoms, and $R^7$ represents alkyl or dialkylamino, each having 1 to 4 carbon atoms in each alkyl part, and optionally substituted phenyl (the preferred substituents being halogen, particularly fluorine, chlorine or bromine, alkyl having 1 to 2 carbon atoms, halogenoalkyl having 1 to 2 carbon atoms and up to 5 halogen atoms, such as, in particular, fluorine atoms and chlorine atoms, trifluoromethyl being mentioned as an example), cyano and nitro.

The following may be mentioned as examples of starting materials of the formula (III): N-fluorodichloromethylsulphenyl-N-phenyl-carbamic acid fluoride, N,N'-bis-(fluorocarbonyl)-thio-bis-methylamine, N-methyl-N-trichloromethylsulphenyl-carbamic acid fluoride, N-methyl-N-fluorodichloromethylsulphenyl-carbamic acid fluoride, N-methyl-N-chlorodifluoromethylsulphenyl-carbamic acid fluoride, N-methyl-N-(3-trifluoromethylphenyl)-sulphenylcarbamic acid fluoride, N-methyl-N-(methoxycarbonylsulphenyl)-carbamic acid fluoride, N-methyl-N-[(3-methylphenyl-sulphenyl)-methylaminosulphenyl)]-carbamic acid fluoride, N-methyl-N-(4-chloro-phenyl)-sulphenyl-carbamic acid fluoride and N-methyl-N-[(4-methylphenyl-sulphenyl)]methylamino-sulphenyl-carbamic acid fluoride, and the corresponding carbamic acid chlorides.

Sulphenylated carbamoyl halides of the formula (III) are known and can be prepared by generally customary and known processes. They can be obtained, for example, by the reaction of the appropriate carbamic acid halides with the appropriate sulphenyl chlorides (see Deutsche Auslegeschrift (German Published Specification) No. 1,297,096, U.S. Pat. No. 3,939,192, and see U.S. Pat. Nos. 3,968,232 and 4,008,328.

Formula (IV) gives a general definition of the oxime-carbamates which are used as starting materials for process variant (b). In formula (IV), $R^1$, $R^2$ and X preferably and particularly preferably represent the substituents which are already mentioned for the N-sulphenylated oxime-carbamates of the formula (I) as preferred and particularly preferred.

$R^{11}$ or $R^{12}$ preferably represent $C_{1-4}$ alkyl, $C_{2-4}$ alkenyl, $C_{2-4}$ alkynyl, $C_{1-4}$ halogenoalkyl having up to 3 halogen atoms, alkoxyalkyl having up to 2 C atoms in each alkyl part and the radical —CO—NH—$R^5$ (in this formula, only one of $R^{11}$ and $R^{12}$ may represent the radical —CO—NH—$R^5$ in each case). $R^5$ preferably represents methyl or ethyl.

$R^{11}$ or $R^{12}$ particularly preferably represent methyl, ethyl, propargyl, allyl or the radical —CO—NH—$R^5$ (only one of $R^{11}$ and $R^{12}$ being permitted to represent —CO—NH—$R^5$).

The oxime-carbamates of the formula (IV) are obtained by a process in which the oximes of the formula (II) are reacted with isocyanates of the general formula $$R^5-N=C=O \tag{VIII}$$

in which $R^5$ has the meaning given above and preferably represents methyl, in an inert organic diluent and, if appropriate, with the addition of a catalyst, such as triethylamine, or of an organic tin compound, such as dibutyl-tin dilaurate.

Hydrocarbons, such as benzene, toluene, cyclohexane or petroleum ether, halogenated hydrocarbons, for example chloroform, methylene chloride or chlorobenzene, ethers, such as diethyl ether, dioxane tetrahydrofuran, ketones, such as acetone or methyl isobutyl ketone, and ethyl acetate may be mentioned as diluents.

The preparation is effected using a molar ratio of the oximes of the formula (II) to the isocyanates of the formula (VIII) of 1:1. An excess of the isocyanates of the formula (VIII) can also preferably be used.

The reaction is effected at temperatures of 0° to 100° C. and, in general, under a pressure of 1 bar.

A previous application U.S. Ser. No. 307,337 filed Sept. 30, 1981, supra, relates to the oxime-carbamates of the formula (IV).

Formula (V) gives a general definition of the sulphenyl chlorides which are additionally required as starting materials for the reaction in process variant (b). In this formula, $R^6$ preferably represents the radicals which have already been mentioned, for the carbonyl halides of the formula (III), as preferred.

The following may be mentioned as examples of starting materials of the formula (V): trichloromethylsulphenyl chloride, dichlorofluoromethylsulphenyl chloride, chlorodifluoromethylsulphenyl chloride, trifluoromethylsulphenyl chloride, phenylsulphenyl chloride, 2,4-dichlorophenylsulphenyl chloride, 3-trifluoromethylphenylsulphenyl chloride, 3-methylphenylsulphenyl chloride, methylsulphenyl chloride, 4-chloro-3-trifluoromethylphenylsulphenyl chloride, methoxycarbonylsulphenyl chloride and ethoxycarbonylsulphenyl chloride.

The sulphenyl chlorides of the formula (V) are generally known compounds of organic chemistry.

The active compounds are well tolerated by plants, have a favorable level of toxicity to warm-blooded animals, and are suitable for combating anthropod pests, especially insects or arachnids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., Locusta migratoria migratorioides, Melanoplus differntialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and Latrodectus mactans;

from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., and Tetranychus spp.

The plant-parasitic nematodes include Pratylenchus spp., *Radopholus similis, Ditylenchus dipsaci, Tylenchulus semipenetrans,* Heterodera spp., Meloidognyne spp., Aphelenchoides spp., Longidorus spp., Xiphinema spp., and Trichodorus spp.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans or fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surfaceactive agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their formulations of the types that are commercially available and in the use forms, prepared from these formulations, as a mixture with other active compounds, such as insecticides, baits, sterilizing agents, acaricides, nemtaticides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present, in their formulations of the types that are commercially available and in the use forms, prepared from these formulations, as a mixture with synergistic agents. Synergistic agents are compounds which increase the action of the active compounds, without it being necessary for the synergistic agent added to be active itself.

The active compound content of the use forms, prepared from the formulations of the types that are commercially available, can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests, especially arthropods (e.g. insects and acarids) and nematodes, which comprises applying to the pests, or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

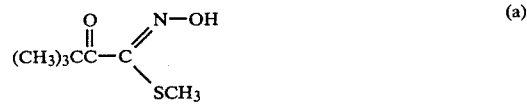

(a)

146 g (1 mol) of 1-methylmercaptopinacoline were mixed with 180 g of 30% strength sodium methylate solution in methanol, and 117.2 g of isoamyl nitrite were added dropwise to the mixture at 0° C., while cooling. The mixture was then allowed to reach room temperature slowly.

The mixture was stirred for a further 4 hours at room temperature, the bulk of the methanol was removed in vacuo, water was added to the residue, aqueous solution was extracted 3 times by shaking with chloroform, the aqueous phase was neutralized with concentrated hydrochloric acid and the product was extracted by shaking with methylene chloride. After the organic phase had been dried over sodium sulphate, the solvent was removed in vacuo and the residue was crystallized using petroleum ether.

Yield: 116 g, (66% of theory), melting point 59°–62° C.

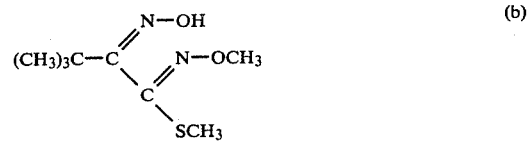

(b)

73.8 g (0.39 mol) of 3,3-dimethyl-1-methoximino-1-methylmercapto-butan-2-one, 81.3 g (1.17 mol) of hydroxylamine hydrochloride and 95.9 g (1.17 mol) of sodium acetate were dissolved in 500 ml of ethanol, and the solution was boiled under reflux for 4 hours. After the same quantity of hydroxylamine hydrochloride and sodium acetate had been added, the reaction mixture was boiled under reflux for a further 4 hours and was then largely freed from solvent in vacuo. Water was added to the residue, the resulting acetic acid was neutralised with sodium bicarbonate solution and the product was extracted with methylene chloride. After the organic phase had been dried over sodium sulphate, the solvent was stripped off in vacuo and the residue was filtered off, after trituration with diisopropyl ether.

Yield: 57.1 g (72% of theory); melting point 137°–138° C.

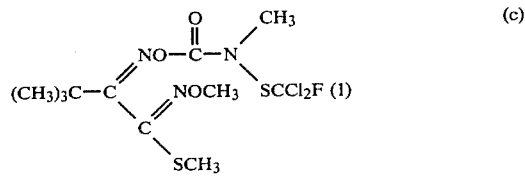

(c)

5.1 g (0.025 mol) of 3,3-dimethyl-1-methyl-mercapto-1-methoximino-2-oximino-butane and 5.25 g (0.025 mol) of N-dichlorofluoromethanesulphenyl-N-methyl-carbamic acid fluoride were dissolved in 100 ml of absolute dioxane, and 2.55 g (0.025 mol) of triethylamine were added dropwise to the solution, while stirring. The mixture was stirred for one hour at 25° C., and was then poured onto 250 ml of water and extracted with methylene chloride. After the extracts had been dried over sodium sulphate, the solvent was removed in vacuo and the residue was stirred with petroleum ether.

Yield 8.5 g (85% of theory); melting point 62°–64° C.

EXAMPLE 2

A mixture composed of 45 g (0.33 mol) of 1-methylthio-1-oximino-propan-2-one, 56 g (0.67 mol) of hydroxylamine methyl ether hydrochloride, 55 g (0.67 mol) of sodium acetate and 400 ml of ethanol was heated under reflux for 2 hours.

The reaction mixture was concentrated to half its volume and was taken up with dilute KOH. The solution was extracted twice with $CHCl_3$. The $H_2O$ phase was then extracted three times with $CHCl_3$, and the extracts were dried over $Na_2SO_4$ and concentrated. Distillation in a bulb tube oven at 150°–170° C./0.3 mm Hg gave approximately 40 g of a viscous oil which was as clear as water and which gradually crystallized out.

Yield: 70% of theory of 1-methylthio-1-oximino-2-methoximino-propane.

Melting point: 52°–74° C.

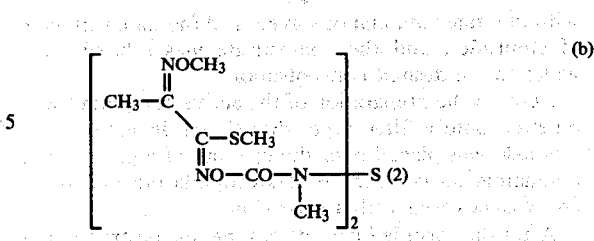

9.3 g (0.09 mol) of triethylamine were added dropwise to 15.5 g (0.09 mol) of 1-methylthio-1-oximino-2-methoximino-propane and 8.4 g (0.045 mol) of N,N'-bis-(fluorocarbonyl)-thio-bis-methylamine in 50 ml of anhydrous dioxane 20°–30° C., while stirring. After the reaction mixture had been stirred for 12 hours at room temperature, it was poured onto ice water and was extracted several times with methylene chloride.

The combined organic phases were dried over sodium sulphate, were concentrated by distilling off the solvent in vacuo and were de-gassed in a high vacuum.

20 g (95% of theory) of N,N'-bis-[1-methylthio-1-oximinocarbonyl-2-methoximino-propane]-thio-bis-methylamine of melting point 96°–102° C. were obtained.

The compounds identified in the following table were obtained by methods analogous to those described in Examples 1 and 2.

TABLE 2

$$R^1-C=NOR^4 \atop R^2X-C=NOR^3 \quad (I)$$

| Compound No. | $R^1$ | $R^2$ | $R^3$ | $R^4$ | $R^6$ | X | Melting point (°C.) or refractive index |
|---|---|---|---|---|---|---|---|
| 3 | $(CH_3)_3$ | $-CH_3$ | $-C_2H_5$ | $-CO-NCH_3-SR^6$ | $CCl_2F$ | S | 1.5108 |
| 4 | $(CH_3)_3$ | $-CH_3$ | $-C_2H_5$ | $-CO-NCH_3-SR^6$ | $CCl_3$ | S | 1.5304 |
| 5 | $(CH_3)_3$ | $-CH_3$ | $-CH_3$ | $-CO-NCH_3-SR^6$ | dimeric | S | 156–157° C. |
| 6 | $(CH_3)_3$ | $-CH_3$ | $-CH_3$ | $-CO-NCH_3-SR^6$ | $CCl_3$ | S | 62–64° C. |
| 7 | $-CH_3$ | $-CH_3$ | $-CONCH_3-SR^6$ | $-CH_3$ | $CCl_3$ | S | 1.5505 |
| 8 | $-CH_3$ | $-C_2H_5$ | $-CONCH_3-SR^6$ | $-CH_3$ | $CCl_3$ | S | 1.5445 |
| 9 | $-CH_3$ | $-CH_3$ | $-CONCH_3-SR^6$ | $-C_2H_5$ | $CCl_3$ | S | 1.5459 |
| 10 | $-CH_3$ | $-CH_3$ | $-CONCH_3-SR^6$ | $-C_2H_5$ | dimeric | S | 1.5309 |
| 11 | $-CH_3$ | $-C_2H_5$ | $-CONCH_3-SR^6$ | $-CH_3$ | dimeric | S | 1.5220 |
| 12 | $-CH_3$ | $-C_2H_5$ | $-CONCH_3-SR^6$ | $-C_2H_5$ | dimeric | S | 1.5198 |
| 13 | $-CH_3$ | $-CH_3$ | $-CH_3$ | $-CO-NCH_3-SR^6$ | dimeric | S | 1.5283 |
| 14 | $-CH_3$ | $-CH_3$ | $-C_2H_5$ | $-CO-NCH_3-SR^6$ | dimeric | S | 1.5284 |
| 15 | $-CH_3$ | $-CH_3$ | $-CH_3$ | $-CO-NCH_3-SR^6$ | $CCl_2F$ | S | 1.5330 |
| 16 | $-CH_3$ | $-CH_3$ | $-CH_3$ | $-CO-NCH_3-SR^6$ | $CCl_3$ | S | 1.5580 |
| 17 | $-CH_3$ | $-CH_3$ | $-CH_2-C\equiv CH$ | $-CO-NCH_3-SR^6$ | $CCl_2F$ | S | 1.5404 |
| 18 | $-CH_3$ | $-CH_3$ | $-C_2H_5$ | $-CO-NCH_3-SR^6$ | $CCl_2F$ | S | 1.5267 |
| 19 | $-CH_3$ | $-CH_3$ | $-CH_2-CH=CH_2$ | $-CO-NCH_3-SR^6$ | $CCl_2F$ | S | 1.5339 |
| 20 | $-CH_3$ | $-CH_3$ | $-CH_2-CH=CH_2$ | $-CO-NCH_3-SR^6$ | dimeric | S | viscous oil |
| 21 | $-CH_3$ | $-CH_3$ | $-CH_2-C\equiv CH$ | $-CO-NCH_3-SR^6$ | dimeric | S | 112° C. |
| 22 | $-CH_3$ | $-CH_3$ | $CONCH_3SR^6$ | $CH_3$ | dimeric | S | |

The pesticidal activity of the compounds of this invention is illustrated by the following examples wherein the compounds according to the present invention are each identified by the number (given in brackets) from Examples 1 and 2 and Table 2 hereinabove.

EXAMPLE 3

Drosophila Test

Solvent: 3 parts of weight of dimethylformamide
Emulsifier: 1 part by weight of alkylaryl polyglycol ether To produce a suitable preparation of active compound, 1 part of weight of active compound was mixed with the stated amount of solvent and the stated amount of emulsifier, and the concentrate was diluted with water to the desired concentration.

1 cm³ of the preparation of the active compound was pipetted onto a filter paper disc (7 cm diameter). The wet disc was placed over the opening of a glass vessel containing 50 vinegar flies (Drosophila melanogaster) and was covered with a glass plate.

After the specified periods of time, the destruction in % was determined. 100% meant that all the flies had been killed; 0% meant that none of the flies had been killed.

In this test, for example, the following compounds showed a superior activity compared with the prior art: (1) and (3).

EXAMPLE 4

Laphygma Test

Solvent: 3 parts of weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (Brassica oleracea) were treated by being dipped into the preparation of active compound of the desired concentration and were infested with caterpillars of the owlet moth (Laphygma frugiperda), as long as the leaves were still moist.

After the specified periods of time, the destruction in % was determined. 100% meant that all the caterpillars had been killed; 0% meant that none of the caterpillars had been killed.

In this test, for example, the following compounds showed a superior activity compared with the prior art: (7), (8), (22), (11), (13), (10), (12), (9), and (15).

EXAMPLE 5

Tetranychus test (resistant)

Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (Phaseolus vulgaris) which were heavily infested with the common spider mite or two-spotted spider mite (Tetranychus urticae) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, for example, the following compounds showed a superior activity compared with the prior art: (15)

EXAMPLE 6

Critical concentration test/soil insects

Test insect: Phorbia antiqua grubs (in the soil)
Solvent: 3 parts of weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and the live test insects. The degree of effectiveness was 100% if all the test insects had been killed and was 0% if just as many test insects were still alive as in the case of the untreated control.

In this test, for example, the following compounds showed a superior action compared with the prior art: (22), (10), (9), (1), (2) and (3).

EXAMPLE 7

Critical concentration test/root-systemic action

Test insect: Myzus persicae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount of weight of active compound per unit volume of soil, which was given in ppm (=mg/l), being decisive. The treated soil was filled into pots and these were planted with cabbage (Brassica oleracea). The active compound could in this way be taken up from the soil by the roots of the plants and be transported into the leaves.

To demonstrate the root-systemic effect, exclusively the leaves were infested with the abovementioned test insects after 7 days. After a further 2 days, the evaluation was made by counting or estimating the dead insects. The root-systemic action of the active compound was deduced from the mortality figures. It was 100% if all the test insects had been killed and 0% if just as many test insects were still alive as in the case of the untreated control.

In the test, for example, the following compounds showed a superior action compared with the prior art: (22), (14), (13), (9), (5), (6), (1), (4), and (3).

EXAMPLE 8

Critical concentration test/root-systemic action

Test insect: Phaedon cochleariae larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount of weight of active compound per unit volume of soil, which was given in ppm (=mg/l), being decisive. The treated soil was filled into pots and these were planted with cabbage (Brassica oleracea). The active compound could in this way be taken up from the soil by the roots of the plants and be transported into the leaves.

To demonstrate the root-systemic effect, exclusively the leaves were infested with the abovementioned test insects after 7 days. After a further 2 days, the evaluation is made by counting or estimating the dead insects. The root-systemic action of the active compound was deduced from the mortality figures. It was 100% if all the test insects had been killed and 0% if just as many test insects were still alive as in the case of the untreated control.

In this test, for example, the following compounds showed a superior action compared with the prior art: (22), (14), (13), (5), (6), (4) and (3).

It will be appreciated that the instant specification and examples are set forth by way of illustration and not limitation, and that various modifications and changes may be made without departing from the spirit and scope of the present invention.

We claim:

1. An N-sulphenylated oxime-carbamate of the formula

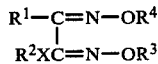

in which
R$^1$ represents alkyl having 1 to 4 carbon atoms, halogenoalkyl having 1 to 4 carbon atoms and up to 5 halogen atoms, cycloalkyl having up to 8 carbon atoms, alkoxyalkyl or alkylthioalkyl having in either case up to 3C atoms in each alkyl part, or optionally substituted phenyl, the substituents(s) being selected from halogen, cyano, nitro and alkyl having 1 to 2 carbon atoms,
R$^2$ represents alkyl having 1 to 4 carbon atoms, alkenyl having 2 to 4 carbon atoms or alkynyl having 2 to 4 carbon atoms, or
R$^1$ and R$^2$ together represent an optionally methyl-substituted methylene, ethylene or propylene bridge,
R$^3$ and R$^4$ each represent alkyl having 1 to 4 carbon atoms, alkenyl having 2 to 4 carbon atoms, alkynyl having 2 to 4 carbon atoms, halogenoalkyl having 1 to 4 carbon atoms and up to 5 halogen atoms, halogenoalkenyl having 2 to 4 carbon atoms and up to 5 halogen atoms or alkoxyalkyl having up to 2 carbon atoms in each alkyl part, or the radical —CO—NR$^5$—S—R$^6$, provided that one of R$^3$ and R$^4$ must represent the radical —CO—NR$^5$—S—R$^6$ in each case,
R$^5$ represents methyl or ethyl, and
R$^6$ represents alkyl having 1 to 4 carbon atoms, halogenoalkyl having 1 to 2 carbon atoms and up to 5 halogen atoms, optionally substituted phenyl (the substituent(s) being selected from halogen, alkyl having 1 to 2 carbon atoms and halogenoalkyl having 1 to 2 carbon atoms and up to 5 halogen atoms), alkoxycarbonyl having 1 to 4 carbon atoms in the alkoxy part, a radical identical to the radical to which the grouping —S—R$^6$ is bonded, or the radical —NR$^8$—SO$_2$—R$^7$,
R$^8$ represents alkyl having 1 to 4 carbon atoms,
R$^7$ represents C$_1$–C$_4$ alkyl, dialkylamino having 1 to 4 carbon atoms in each alkyl part, or optionally substituted phenyl, the substituent(s) being selected from halogen, alkyl having 1 to 2 carbon atoms, halogenoalkyl having 1 to 2 carbon atoms and up to 5 halogen atoms, cyano and nitro, and X represents O or S.

2. An N-sulphenylated oxime-carbamate according to claim 1, in which
R' represents methyl, isopropyl, tert.-butyl, fluoro-tert.-butyl, chloro-tert.-butyl, difluoro-tert.-butyl or dichloro-tert.-butyl,
R$^2$ represents methyl or ethyl, or
R$^1$ and R$^2$ together represent an ethylene bridge;
R$^3$ and R$^4$ each represent methyl, ethyl, allyl or propargyl, or CO—N(CH$_3$)—S—R$^6$, provided that one of
R$^3$ and R$^4$ must represent —CO—N(CH$_3$)—S—R$^6$,
R$^6$ represents trichloromethyl, dichlorofluoromethyl, phenyl which is substituted by halogenoalkyl or by alkyl, or the identical radical to which the grouping S—R$^6$ is bonded, and X represents S.

3. An insecticidal and acaricidal composition comprising an insecticidally and acaricidally effective amount of a compound according to claim 11 and a diluent.

4. A method of combating insects and acarids which comprises applying to such insects and acarids or to an insect and acarid habitat an insecticidally and acaricidally effective amount of a compound according to claim 1.

* * * * *

UNITED STATES PATENT AND TRADEMARK OFFICE
CERTIFICATE OF CORRECTION

PATENT NO. : 4,470,984
DATED : September 11, 1984
INVENTOR(S) : Johannes Schmetzer, et al It is certified that error appears in the above-identified patent and that said Letters Patent is hereby corrected as shown below:

Col. 5, line 4, Col. 7, line 4, Col. 9, line 4, Col. 11, line 4, Col. 13, line 4 and Col. 15, line 4

Insert heading as follows:
-- $R^1$   $R^2$   $R^3$   $R^4$   $R^6$ --

Col. 19, line 14

Correct spelling of --trifluoromethyl--

Col. 22, line 34

Insert -- - -- between "surface" and "active"

Col. 28, line 42

Before "weight" delete "of" and substitute --by--

Col. 30, line 48

After "claim" delete "11" and substitute --1--

Signed and Sealed this

Twenty-sixth Day of February 1985

[SEAL]

Attest:

DONALD J. QUIGG

Attesting Officer

Acting Commissioner of Patents and Trademarks